United States Patent [19]

Förster et al.

[11] Patent Number: 4,784,682
[45] Date of Patent: Nov. 15, 1988

[54] 6-CHLOROBENZAZOLYLOXYACETA-MIDES

[75] Inventors: Heinz Förster; Volker Mues, both of Wuppertal; Robert R. Schmidt, Bergisch-Gladbach; Hans-Joachim Santel, Cologne; Gerd Hänssler; Ludwig Eue, both of Leverkusen, all of Fed. Rep. of Germany

[73] Assignee: Bayer Aktiengesellschaft, Leverkusen, Fed. Rep. of Germany

[21] Appl. No.: 55,102

[22] Filed: May 28, 1987

Related U.S. Application Data

[63] Continuation-in-part of Ser. No. 731,233, May 6, 1985, abandoned.

[30] Foreign Application Priority Data

May 16, 1984 [DE] Fed. Rep. of Germany ....... 3418168

[51] Int. Cl.$^4$ ..................... A01N 43/76; A01N 43/78; C07D 263/58; C07D 277/68
[52] U.S. Cl. ........................ 71/88; 548/221; 514/375
[58] Field of Search ............. 71/88; 548/221; 514/372

[56] References Cited

U.S. PATENT DOCUMENTS 4,384,881 5/1983 Kayama et al. ............. 71/88
4,509,971 4/1985 Forster et al. ............. 71/94

FOREIGN PATENT DOCUMENTS 0005501 11/1979 European Pat. Off. ........ 71/90
037527 3/1981 European Pat. Off. ........ 71/88
3038652 5/1982 Fed. Rep. of Germany .... 71/94

Primary Examiner—Richard L. Raymond
Assistant Examiner—Patricia L. Morris
Attorney, Agent, or Firm—Sprung Horn Kramer & Woods

[57] ABSTRACT

Herbicidally and fungicidally active novel 6-chlorobenzazolyloxyacetanilides of the formula

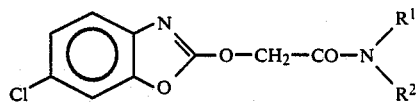

in which
$R^1$ is alkyl with 1 to 6 carbon atoms, and
$R^2$ is phenyl which is optionally mono-, di- or tri-substituted by methyl or ethyl.

17 Claims, No Drawings

6-CHLOROBENZAZOLYLOXYACETAMIDES

This is a continuation-in-part of Application Ser. No. 731,233, filed May 6, 1985, now abandoned.

The invention relates to new 6-chlorobenzazolyloxyacetamides, a process for their preparation and their use as herbicides and fugicides.

It is already known that certain benzazolyloxyacetamides, such as, for example, 2-(benzothiazol-2-yl)N-methyl-oxyacetanilide, have herbicidal properties, in particular selective herbicidal properties (compare, for example, DE-OS (German Published Specification) No. 2,903,966 and EP-OS (European Published Specification) No. 5,501). Moreover, certain 5-chlorobenzoxazolyloxyacetamides have also been disclosed as herbicides (compare DE-OS (German Published Specification) No. 3,038,652).

However, the herbicidal action of these previously known compounds against weeds and their tolerance towards important crop plants is not always completely satisfactory in all fields of use, especially when low amounts are applied and low concentrations are used.

New 6-chlorobenzazolyloxyacetamides of the general formula (I)

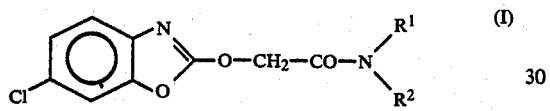

in which
X represents oxygen or sulphur and
R¹ and R² independently of one another represent alkyl, alkenyl of alkinyl, or represent in each case optionally substituted cycloalkyl or cycloalkenyl, or represent halogenoalkyl, alkoxyalkyl, alkoxyalakyleneoxy or alkoxy, or represent aralkyl or optionally substituted aryl, or
R¹ and R², together with the nitrogen atom to which they are bonded, represent an optionally substituted, saturated or unsaturated heterocyclic radical, which can contain further hetero-atoms,
have been found.

It has furthermore been found that the new 6-chlorobenzazolyloxyacetamides of the general formula (I) are obtained by a process in which 6-chlorobenzazoles of the formula (II)

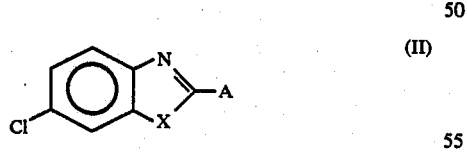

in which
X has the abovementioned meaning and
A represents an electron-withdrawing leaving grouping,
are reacted with glycolic acid amides of the formula (III)

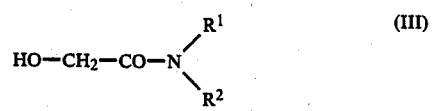

in which
R¹ and R² have the abovementioned meaning,
if appropriate in the presence of a diluent and if appropriate in the presence of an acid-binding agent, and if appropriate in the prsence of a catalyst.

Finally, it has been found that the new 6-chlorobenzazolyloxyacetamides of the formula (I) have herbicidal properties, in particular also selective herbicidal properties, and moreover also have fungicidal properties.

Surprisingly, the new 6-chlorobenzazolyloxyacetamides of the formula (I) have a considerably improved herbicidal activity against widespread weeds which are difficult to combat, coupled with a comparably high tolerance towards important crop plants and at the same time also a better fungicidal activity in comparison with the benzazolyloxyacetamides previously known from the prior art, such as, for example, N-methyl-2-benzothiazolyloxyacetanilide, which are closely related compounds chemically and from the point of view of their action.

Formula (I) provides a general definition of the 6-chlorobenzazolyloxyacetamides according to the invention. Preferred compounds of the formula (I) are those in which
X represents oxygen or sulphur and
R¹ and R² independently of one another represent straight-chain or branched alkyl with 1 to 8 carbon atoms or straight-chain or branched alkenyl and alkinyl with in each case 2 to 8 carbon atoms, or represent cycloalkyl or cycloalkenyl with in each case 3 to 7 carbon atoms, optionally monosubstituted or polysubstituted by identical or different substituents, particularly possible substituents being alkyl radicals with 1 to 4 carbon atoms, or represent in each case straight-chain or branched alkoxy, alkoxyalkylenoxy or alkoxyalkyl with in each case 1 to 8 carbon atoms in the individual alkyl or alkylene parts, or represent halogenoalkyl with 1 to 8 carbon atoms and 1 to 5 halogen atoms, in particular fluorine, chlorine and bromine, or represent aralykyl with 6 to 10 carbon atoms in the aryl part and 1 to 2 carbon atoms in the alkyl part, or represent aryl which has 6 to 10 carbon atoms and is optionally monosubstituted or polysubstituted by identical or different substtuents, possible substituents being: halogen, straight-chain or branched alkyl, alkoxy or alkylthio with in each case 1 to 4 carbon atoms, halogenoalkyl, haolgenoalkoxy anad halogenoalkylthio with in each case 1 or 2 carbon atoms and 1 to 5 halogen atoms, in particular flurioine, chlorine and bromine, and nitro, or
R¹ and R², together with the nitrogen atom to which they are bonded, represent a saturated or unsaturated, 5-membered to 7-membered heterocyclic radical which is optionally monosubstituted or polysubstituted by identical or different substituents, possible substituents being: straight-chain or branched alkyl with 1 to 6 carbon atoms, also in the form of a fused-on ring system, aryl with 6 to 10 carbon atoms, also in the form of a fused-on ring system, or dioxyalkylene with 2 or 3 carbon atoms.

Particularly preferred compounds of the formula (I) are those
in which
X represents oxygen or sulphur and
R¹ and R² independently of one another represent straight-chain or branched alkyl with 1 to 6 carbon atoms, or represent straight-chain or branched alkenyl and alkinyl with in each case 2 to 6 carbon atoms, or represent cycloalkyl or cycloalkenyl which has 5 to 7 carbon atoms and is optionally mono-, di- or tri-substituted by identical or different radicals from the group comprising methyl and ethyl, or represent in each case straight-chain or branched alkoxy, alkoxyalkylenoxy or alkoxyalkyl with in each case 1 to 6 carbon atoms in the individual alkyl parts, or represent halogenoalkyl with 1 to 6 carbon atoms and 1 to 5 halogen atoms, in particular fluorine, bromine and chlorine, or represent benzyl, or represent phenyl which is optionally mono-, di- or tri-substituted by identical or different substituents, particularly preferred substituents being: methyl, ethyl, methoxy, methylthio, trifluoromethyl, trifluoromethoxy, trifluoromethylthio, fluorine, chlorine or nitro; or $R^1$ and $R^2$, together with the nitrogen atom to which they are bonded, represent a heterocyclic radical of the formula

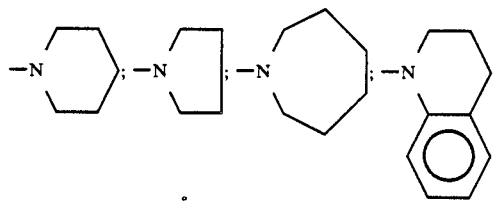

which is optionally mono-, di or tri-substituted by identical or different substituents, particularly preferred substituents being: methyl, ethyl and phenyl.

Most preferred are those compounds in which $R^1$ is alkyl with 1 to 3 carbon atoms, and $R^2$ is phenyl, methylphenyl or dimethlyphenyl.

The following compounds of the general formula (I) may be mentioned specifically, in addition to the compounds mentioned in the preparation examples:

TABLE 1

| X | $R^1$ | $R^2$ | or $-N\begin{smallmatrix}R^1\\R^2\end{smallmatrix}$ |
|---|---|---|---|
| O | CH₃ | CH₃O—CH₂— | |
| O | CH₃ | (cyclohexyl-H) | |
| O | CH₃ | (cyclohexenyl) | |
| O | CH₃ | F₃C—CH₂— | |
| O | CH₃ | (2-methylphenyl) | |
| O | CH₃ | (nitro-methylphenyl) | |
| O | CH₃ | (4-trifluoromethylphenyl) | |
| O | C₂H₅ | CH₂=CH—CH₂— | |
| O | CH₂=CH—CH₂— | CH₂=CH—CH₂— | |

TABLE 1-continued $$\text{Cl-benzoxazole(X)-O-CH}_2\text{-CO-N}R^1R^2 \quad (I)$$

| X | R¹ | R² | or —N(R¹)(R²) |
|---|-----|-----|---------------|
| O | | | 3,5-dimethylpiperidin-1-yl |
| O | | | 4-methylpiperidin-1-yl |
| O | | | 1,2,3,4-tetrahydroquinolin-1-yl |
| O | | | 3-ethylpiperidin-1-yl |
| O | CH₃ | HC≡C—CH₂— | |
| O | CH₃O | C₂H₅—CH(CH₃)— | |
| O | (CH₃)₂CHO— | C₂H₅O—CH₂CH₂—O— | |
| O | CH₃ | 3-chlorophenyl | |
| O | CH₃ | 3-(trifluoromethyl)phenyl | |
| S | CH₃ | CH₃O—CH₂— | |
| S | CH₃ | HC≡C—CH₂— | |
| S | CH₃ | cyclohexyl | |
| S | CH₃ | cyclohex-3-en-1-yl | |

TABLE 1-continued
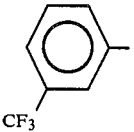
| X | R¹ | R² | or | 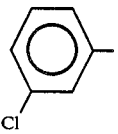 |
|---|---|---|---|---|
| S | CH₃ | F₃C—CH₂— | | |
| S | CH₃ | 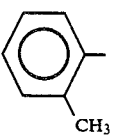 | | |
| S | CH₃ | 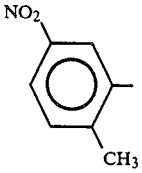 | | |
| S | CH₃ | 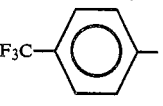 | | |
| S | CH₃ | 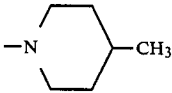 | | |
| S | CH₃— | 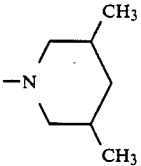 | | |
| S | CH₃O— | C₂H₅—CH—<br>        \|<br>       CH₃ | | |
| S | (CH₃)₂CHO— | (CH₃)₂CH— | | |
| S | C₂H₅ | CH₂=CH—CH₂— | | |
| S | CH₂=CH—CH₂— | CH₂=CH—CH₂— | | |
| S | | | | —N⟨piperidine-4-CH₃⟩ |
| S | | | | —N⟨piperidine-3,5-di-CH₃⟩ |

TABLE 1-continued $$\underset{Cl}{\text{benzoxazole-Cl}} \overset{N}{\underset{X}{\bigcirc}} -O-CH_2-CO-N\overset{R^1}{\underset{R^2}{}} \quad (I)$$

| X | $R^1$ | $R^2$ | or $-N\overset{R^1}{\underset{R^2}{}}$ |
|---|---|---|---|
| S | | |  |
| S | | | 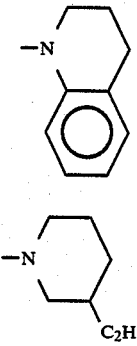 |
| S | | | 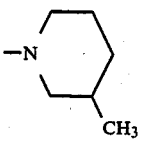 |
| O | | | 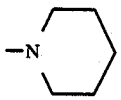 |
| S | | | 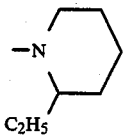 |
| O | | | 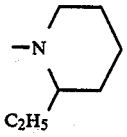 |
| O | $CH_3-$ | $CH_2=CH-CH_2-$ | |
| S | $CH_3-$ | $CH_2=CH-CH_2-$ | |
| O | $CH_3O-CH_2-$ | $C_2H_5-CH-$<br>$\quad\quad\quad\;\; \mid$<br>$\quad\quad\quad\;\; CH_3$ | |
| S | $CH_3O-CH_2-$ | $C_2H_5-CH-$<br>$\quad\quad\quad\;\; \mid$<br>$\quad\quad\quad\;\; CH_3$ | |
| O | $CH_3(CH_2)_3-$ | $CH_3(CH_2)_3-$ | |
| S | $CH_3(CH_2)_3-$ | $CH_3(CH_2)_3-$ | |
| O | $C_2H_5-$ | $(CH_3)_2CH-$ | |
| S | $C_2H_5-$ | $(CH_3)_2CH-$ | |
| O | $(CH_3)_2CH-$ | $C_2H_5OCH_2CH_2-O-$ | |
| S | $(CH_3)_2CH-$ | $C_2H_5OCH_2CH_2-O-$ | |
| O | $CH_3-$ | 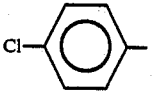 | |

TABLE 1-continued $$\text{(I)} \quad \underset{Cl}{\text{benzoxazole}}\text{-O-CH}_2\text{-CO-N}\underset{R^2}{\overset{R^1}{\diagup}}$$

| X | R¹ | R² or $-N\underset{R^2}{\overset{R^1}{\diagup}}$ |
|---|---|---|
| S | CH₃— | 4-Cl-C₆H₄— |
| S | CH₃— | 4-F-C₆H₄— |
| S | CH₃— | 3-F-C₆H₄— |
| O | CH₃— | 4-F-C₆H₄— |
| O | CH₃— | 1,2,3,4-tetrahydroquinolin-1-yl |
| S | CH₃— | 4-CH₃S-C₆H₄— |
| O | CH₃— | 4-CH₃S-C₆H₄— |
| S | CH₃— | 3-CH₃S-C₆H₄— |
| S | CH₃— | 4-O₂N-C₆H₄— |
| O | CH₃— | 4-O₂N-C₆H₄— |
| O | CH₃— | n-H₉C₄— |
| S | CH₃— | n-H₉C₄— |

TABLE 1-continued $$\text{(I)} \quad \underset{Cl}{\underset{|}{\bigcirc}}\!\!\!\!\!\!\!\!\overset{N}{\underset{X}{\bigcirc}}\!\!-O-CH_2-CO-N\!\!<\!\!\overset{R^1}{R^2}$$

| X | R$^1$ | R$^2$ | or | $-N\!\!<\!\!\overset{R^1}{R^2}$ |
|---|---|---|---|---|
| O | | | | 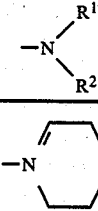 |
| S | | | |  |
| O | | | |  |
| S | | | |  |
| O | C$_2$H$_5$— | CH$_2$=CH— | | |

If, for example, 2,6-dichlorobenzoxazole and glycolic acid N-methylanilide are used as starting substances, the course of the reaction in the process according to the invention can be represented by the following equation:

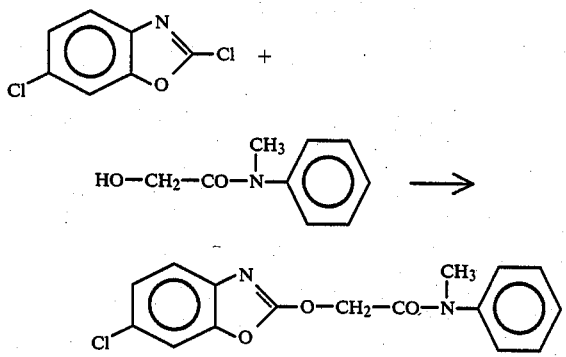

Formula (II) provides a general definition of the 6-chlorobenzazoles required as starting substances for carrying out the process according to the invention. In this formula (II), X preferably represents oxygen or sulphur and A preferably represents halogen, in particular chlorine or bromine, or alkylsulphonyl or aralkylsulphonyl, in particular methylsulphonyl or ethylsulphonyl.

The 6-chlorobenzazoles of the formula (II) are known (compared for example EP-OS (European Published Specification) No. 43,573 and DE-OS (German Published Specification) No. 3,025,910, or they can be prepared in a simple manner by methods analogous to those known in principle.

Formula (III) provides a general definition of the glycolic acid amides also required as starting substances for carrying out the process according to the invention. In this formula (III), R$^1$ and R$^2$ preferably represent those radicals which have already been mentioned as preferred for these substituents in the description of the substances of the formula (I) according to the invention. The glycolic acid amides of the formula (III) are likewise known (compare, for example, DE-OS (German Published Specification) No. 2,904,490, EP-OS (European Published Specification) No. 5,501, EP-OS (European Published Specification) No. 29,171, DE-OS (German Published Specification) No. 3,038,598 and DE-OS (German Published Specification No. 3,244,956).

Possible diluents for the process according to the invention are organic or inorganic solvents. Preferred solvents are hydrocarbons, such as toluene or cyclohexane, halogenahydrocarbons, such as methylene chloride, chloroform, dichloroethane or chlorobenzene, ketones, such as acetone or methyl isobutyl ketone, ethers such as diethyl ether, diisopropyl ether or methyl t-butyl ether, alcohols, such as methanol, ethanol or isopropanol, amides, such as dimethylformamide or dimethylacetamide, sulphoxides, such as dimethylsulphoxide, water or aqueous salt solutions.

Salts which are preferably used here are chlorides or sulphates of alkali metals or alkaline earth metals, such as, for example, sodium chloride, potassium chloride or calcium chloride. Sodium chloride is particularly preferred.

The process according to the invention is advantageously carried out using acid-binding agents. The preferred acid-binding agents used are strongly basic alkali metal and alkaline earth metal compounds, for example oxides, magnesium oxide and calcium oxide, hydroxides, such as, for example, sodium hydroxide, potassium hydroxide, magnesium hydroxide and calcium hydroxide, and/or carbonates, such as, for example, sodium carbonate, potassium carbonate, magnesium carbonate and calcium carbonate.

It may in some cases prove advantageous to add 0.01 to 10% by weight (based on the glycolic acid amide of the formula (III) employed) of a phase transfer catalyst. Examples of such catalysts which may be mentioned are: tetrabutylammonium chloride, tetrabutylammonium bromide, tributyl-methylphosphonium bromide, trimethyl-$C_{13}$/$C_{15}$-alkyl-ammonium chloride, dibenzyl-dimethyl-ammoniummethylsulphate, sulphate, dimethyl-C12/C14-alkyl-benzyl-ammonium chloride, tetrabutylammoniumhydroxide, 18-crown-6, triethyl-benzylammonium chloride, trimethylbenzylammonium chloride and tetraethylammonium bromide.

The reaction temperatures can be varied within a substantial range in the process according to the invention. They are in general between $-50°$ C. and $+100°$ C., preferably between $-20°$ C. and $+100°$ C.

The process according to the invention is in general carried out under normal pressure, but it can also be carried out under increased or reduced pressure, for example between 0.1 and 10 bar.

For carrying out the process according to the invention, in general 0.1 to 10 moles, preferably 0.8 to 1.2 moles, of glycolic acid amide of the formula (III) and 0.5 to 10 moles, preferably 0.5 to 3 moles, of base are employed per mole of 6-chlorobenzazole of the formula (II). The sequence in which the reactants are added can be changed as desired, and it is also possible to meter all the components simultaneously into the reaction vessel. The reaction procedure can be continuous or discontinuous. Working up is affected in the customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for examle, in connection with the following plants:

Dicotyledon weeds of the genera:
Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis Papaver and Centaurea.

Dicotyledon cultures of the genera:
Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:
Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Schipus, Paspalum, Ischaemum, Sphenoclea, Dactyloctenium, Agrostis, Alopecurus and Apera.

Monocotyledon cultures of the genera:
Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palam plantations, cocoa plantations, soft fruit plantings and hopfields, and for the selective combating of weeds in annual cultures.

Besides an outstanding action against harmful plants, the active compounds according to the invention also exhibit a good tolerance towards important crop plants, and they can therefore be employed as selective agents for combating weeds in monocotyledon crops, such as cereals and rice, and also in dicotyledon crops, such as soy bean, cotton, sugar beet and the like.

The active compounds according to the invention moreover also exhibit a powerful microbicidal action when appropriate amounts are applied, and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating rice diseases, such as, for example, against the rice spot disease causative organism (*Pyricularia oryzae*). Besides a protective activity, the active compounds according to the invention also exhibit, in particular, systemic properties here.

The active compounds can be converted to the customary formulations, such as solutions, emulsions, suspensions, powders, foams, pastes, granules, aerosols, natural and synthetic materials impregnated with active compounds, very fine capsules in polymeric substances and in coating compositions for seed, and in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surfaceactive agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents ther are suitable: for example ligninsulphite waste liquors and methylcellulose.

Adhesives such as carboxmethylcellulose and natural and synthetic polymers in the form of powders, granules, or latices, such as gum arabic, polyvinyl alcohol and plyvinyl acetate, as well as natural phospholipids, such as cephalins and lecithins, and synthetic phospholipids, can be used in the formulations. Other additives can be mineral and vegetable oils.

It is possible to use colorants such asa inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beets and 4-amino-6-(1,2-dimethylethyl)-3-methylthio-1,2,4-triazin-5(4H)-one for combating weeds in soy beans. Mixtures with N,N-dimethyl-N'-(4-chloro-3-methylphenyl)-urea or N,N-dimethyl-N'-(4-isopropylphenyl)-urea, or with other triazinediones or pyridyl-phenoxy-propionic acids are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used inthe customary manner, for example by watering, spraying, atomizing or scattering.

The active compounds according to the invention can be applied either before or after emergence of the plants.

They can also be incorporated into the soil before sowing.

The amount of active compounds used can vary within a substantial range. It depends essentially on the nature of the desired effect. In general, the amounts used for application as herbicides are between 0.01 and 10 kg of active compound per hectare of soil surface, preferably between 0.05 and 5 kg per ha.

When used as fungicides, the active compounds according to the invention can likewise be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 adn 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The following examples serve to further illustrate the invention.

PREPARATION EXAMPLES

EXAMPLE 1

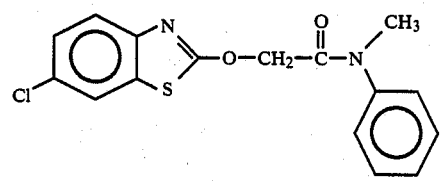

A solution of 4 g (0.02 mole) of 2,6-dichlorobenzothiazol in 10 ml of acetonitrile is added to a mixture of 3.3 g (0.02 mole) of glycolic acid N-methylanilide and 1.2 g (0.02 mole) of powdered potassium hydroxide in 50 ml of isopropanol at −15° C. and, when the addition has ended, the mixture is stirred at −5° C. for a further 15 hours. For working up, the reaction mixture is poured into water and the solid precipitated is filtered off with suction, rinsed with water, dried and crystallized from a mixture of acetic acid/petroleum ether (1:1). 4 g (75% of theory) of 2-(6-chlorobenzothiazol-2-yl)-N-methyl-oxy acetanilide of melting point 108° C. are obtained.

EXAMPLE 2

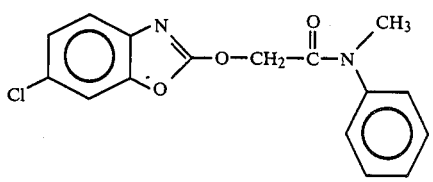

A solution of 9.4 g (0.05 mole) of 2,6-dichlorobenzoxazole in 20 ml of isopropanol is added dropwise to a mixture of 8.2 g (0.05 mole) of glycolic acid N-methylanilide and 3.1 g (0.05 mole) of powdered potassium hydroxide in 80 ml of isopropanol at −10° C., with stirring, and, when the addition has ended, the mixture is stirred at −5° C. for a further 15 hours. For working up, the reaction mixture is poured into water and the solid precipitate is filtered off with suction, rinsed with water and dried.

13 g (82% of theory) of 2-(6-chlorobenzoxazol-2-yl)-N-methyloxyacetanilide of melting point 139° C. are obtained.

The following compounds of the general formula (I) are obtained in a corresponding manner and in accordance with the general preparation statements.

TABLE 2

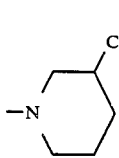

| Example No. | $R^1$ | $R^2$ | or $-N\binom{R^1}{R^2}$ | X | Melting point |
|---|---|---|---|---|---|
| 3 | $CH_3$ | $CH_3(CH_2)_3-$ | | O | 78–79° C. |
| 4 | | | 2-methylpiperidinyl | O | 112° C. |
| 5 | | | 2-methylpiperidinyl | O | 82° C. |
| 6 | | | hexamethyleneimino | O | 118° C. |
| 7 | $C_2H_5$ | $C_2H_5$ | | O | 80° C. |
| 8 | $CH_3$ | $CH_3$ | | O | |
| 9 | $CH_3(CH_2)_2-$ | $CH_3(CH_2)_2-$ | | O | |
| 10 | $CH_3$ | cyclohexenyl | | O | |
| 11 | $CH_3$ | $CH_3$ | | S | 160° C. |
| 12 | $C_2H_5$ | $C_2H_5$ | | S | 76° C. |
| 13 | $CH_3$ | $CH_3(CH_2)_3-$ | | S | 94° C. |
| 14 | $CH_3(CH_2)_2-$ | $CH_3(CH_2)_2-$ | | S | 71° C. |
| 15 | $CH_3$ | cyclohexenyl | | S | |

TABLE 2-continued $$\text{(I)} \quad \text{Cl-benzoxazole}-O-CH_2-C(=O)-N(R^1)(R^2)$$

| Example No. | R$^1$ | R$^2$ or $-N(R^1)(R^2)$ | X | Melting point |
|---|---|---|---|---|
| 16 | | 2-methylpiperidin-1-yl | S | 78° C. |
| 17 | | 3-methylpiperidin-1-yl | S | 98° C. |
| 18 | | azepan-1-yl (hexamethyleneimino) | S | 84° C. |
| 19 | CH$_2$=CH—CH$_2$— | CH$_2$=CH—CH$_2$— | S | 70° C. |
| 20 | | 4-methylpiperidin-1-yl | S | 88° C. |
| 21 | CH$_3$O— | C$_2$H$_5$—CH(CH$_3$)— | S | |
| 22 | CH$_3$ | 3-(trifluoromethyl)phenyl | S | 144° C. |
| 23 | CH$_3$ | CH≡C—CH$_2$— | S | 115° C. |
| 24 | | 1,2,3,6-tetrahydropyridin-1-yl | S | 142° C. |
| 25 | | 1,2,3,4-tetrahydroquinolin-1-yl | S | 162° C. |
| 26 | CH$_3$ | CH$_3$(CH$_2$)$_2$— | S | |
| 27 | CH$_3$ | CH$_3$OCH$_2$— | S | 77° C. |
| 28 | CH$_3$ | 3-chlorophenyl | S | 123° C. |

TABLE 2-continued $$\text{(I)} \quad \underset{Cl}{\text{6-Cl-benzo}[X]\text{azole}}-O-CH_2-\overset{O}{\underset{\|}{C}}-N\underset{R^2}{\overset{R^1}{\diagdown}}$$

| Example No. | $R^1$ | $R^2$ | or $-N\underset{R^2}{\overset{R^1}{\diagdown}}$ | X | Melting point |
|---|---|---|---|---|---|
| 29 | $CH_3$ | 2-methylphenyl | | S | 126° C. |
| 30 | $CH_3(CH_2)_3-$ | $CH_3(CH_2)_3-$ | | S | 67° C. |
| 31 | $C_2H_5-$ | $CH_2=CH-$ | | S | 78° C. |
| 32 | $CH_2=CH-CH_2-$ | $CH_2=CH-CH_2-$ | | O | 82° C. |
| 33 | $CH_3$ | cyclohex-1-enyl | | O | 65° C. |
| 34 | $(CH_3)_2CH-$ | $C_2H_5-O-CH_2-CH_2-O-$ | | O | $n_D^{20} = 1.5274$ |
| 35 | $CH_3$ | $-C_4H_9(-sec.)$ | | O | 79° C. |
| 36 | | | $-N\diagup\diagdown-CH_3$ (4-methylpiperidinyl) | O | 98° C. |
| 37 | $CH_3$ | $CH_3$ | | O | 120° C. |
| 38 | $CH_3-(CH_2)_2-$ | $CH_3-(CH_2)_2-$ | | O | 59° C. |
| 39 | | | $-N\diagup\diagdown$ with $C_2H_5$ (2-ethylpiperidinyl) | O | 86° C. |

EXAMPLE 4

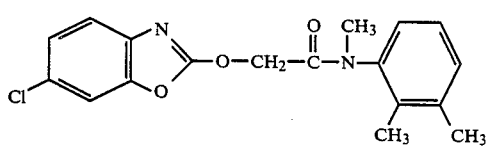

A solution of 10,1 g (0.05 mole) of 2,6-dichlorobenzoxazole in 20 ml of acetonitrile is added slowly, at −20° C., to a mixture of 9.6 g (0.05 mole) of glycolic acid N-methyl-2,3-dimethylanilide and 3.1 g (0.05 mole) of powdered potassium hydrixide in 100 ml of isopropanol. The mixture is subsequently stirred at −20° C. for 12 hours. For working up, the reaction mixture is poured on to water and the solid precipitated is filtered off, rinsed with water and dried.

11g (65 % of theory) of 2-(6-chlorobenzoxazol-2-yl)-N-methyloxyacet-2,3-dimethylanilide with a melting point of 138° C. are obtained.

The following compounds of the general formula (I) can also be prepared in a corresponding manner and in accordance with the general preparative specifications:

TABLE 3

$$\text{(I)} \quad \underset{Cl}{\text{6-Cl-benzo}[X]\text{azole}}-O-CH_2-CO-N\underset{R^2}{\overset{R^1}{\diagdown}}$$

| Example No. | $R^1$ | $R^2$ | X | Melting point |
|---|---|---|---|---|
| 41 | $C_2H_5$ | phenyl | O | 152° C. |
| 42 | $C_3H_7-n$ | phenyl | O | 63° C. |
| 43 | $C_3H_7-i$ | phenyl | O | |

TABLE 3-continued

![Structure I: Cl-benzoxazole-O-CH₂-CO-NR¹R²]

Structure (I):
5-Cl-benzo[X]azol-2-yl-O-CH₂-CO-NR¹R²

| Example No. | R¹ | R² | X | Melting point |
|---|---|---|---|---|
| 44 | CH₃ | 4-CH₃-phenyl | O | 114° C. |
| 45 | CH₃ | 3-CH₃-phenyl | O | 53° C. |
| 46 | C₂H₅ | 3-CH₃-phenyl | O | 52° C. |
| 47 | CH₃ | 2-CH₃-phenyl | O | 136° C. |

USE EXAMPLES

The compound shown below is used as a comparison substance in the folowing use examples:

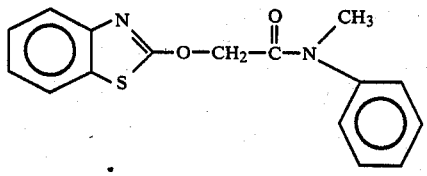

(A)

2-(Benzothiazol-2-yl)-N-methyl-oxyacetanilide (known from DE-OS (German Published Specification) No. 2,903,966 and European Pat. No. 5,501).

The following compound is also used as a comparison substance in Example A:

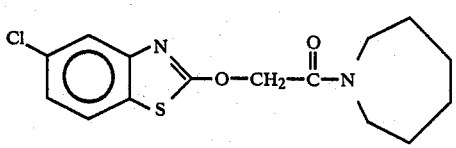

(B)

2-(5-Chlorobenzothiazol-2-yl)-N,N-hexamethylene-oxyacetamide (known from DE-OS (German Published Specification) No. 3,038,652).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior herbicidal activity with a comparable selectivity for useful plants in relation to the prior art is shown, for example, by the compounds according to the following preparation examples: 3 and 6.

EXAMPLE B

Post-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0 % = no action (like untreated control)
100 % = total destruction

In this test, a clearly superior activity compared with the prior art is shown, for example, by the compound according to preparation Example 6.

EXAMPLE C

Pyricularia test (rice)/systemic

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which yound rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C.

and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 3, 6 and 7.

It will be appreciated the the instant specification and examples are set forth by way of illustration and not limitation, and that various modifications and changes may be made without departing from the spirit and scope of the present invention.

What is claimed is:

1. A 6-chlorobenzazolyl-oxyacetanilide of the formula

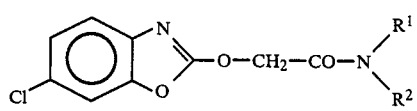

in which
R¹ is alkyl with 1 to 6 carbon atoms, and
R² is phenyl which is optionally mono-, di- or tri-substituted by methyl or ethyl.

2. A compound according to claim 1, in which
R¹ is alkyl with 1 to 3 carbon atoms, and
R² is phenyl, methylphenyl or dimethylphenyl.

3. A compound according to claim 1, wherein such compound is 2-(6-chlorobenzoxazol-2-yl)-N-methyl-oxyacet-2,3-dimethyl-anilide of the formula

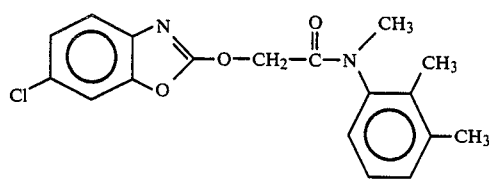

4. A compound according to claim 1, wherein such compound is 2-(6-chlorobenzoxazol-2-yl)-N-methyl-oxyacetanilide of the formula

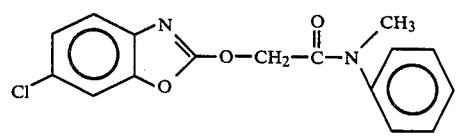

5. A compound according to claim 1, wherein such compound is 2-(6-chlorobenzoxazol-2-yl)-N-ethyl-oxyacet-anilide of the formula

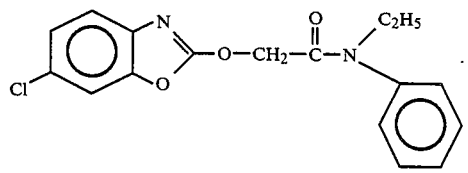

6. A compound according to claim 1, wherein such compound is 2-(6-chlorobenzoxazol-2-yl)-N-n-propyl-oxyacet-2,3-cimethyl-anilide of the formula

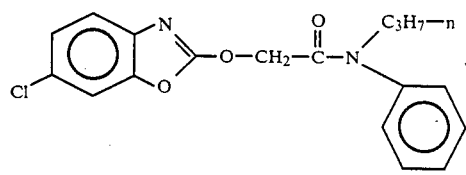

7. A compound according to claim 1, wherein such compound is 2-(6-chlorobenzoxazol-2-yl)-N-i-propyl-oxyacet-anilide of the formula

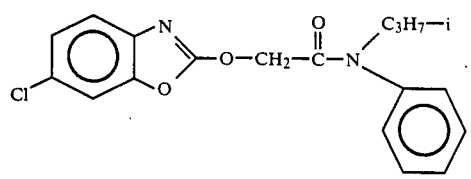

8. A compound according to claim 1, wherein such compound is 2-(6-chlorobenzoxazol-2-yl)-N-methyl-oxyacet-4-methyl-anilide of the formula

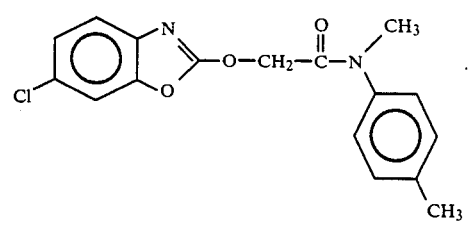

9. A compound according to claim 1, wherein such compound is 2-(6-chlorobenzoxazol-2-yl)-N-methyl-oxyacet-3-methyl-anilide of the formula

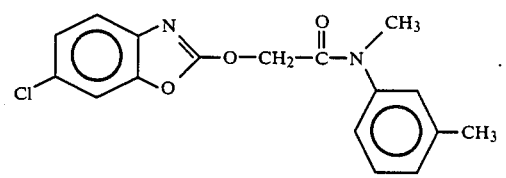

10. A compound according to claim 1, wherein such compound is 2-(6-chlorobenzoxazol-2-yl)-N-ethyl-oxyacet-3-methyl-anilide of the formula

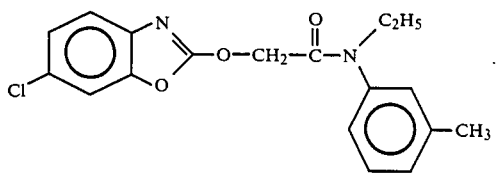

11. A compound according to claim 1, wherein such compound is 2-(6-chlorobenzoxazol-2-yl)-N-methyl-oxyacet-2-methyl-anilide of the formula

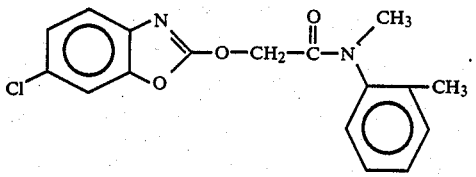

12. A herbicidal or fungicidal composition comprising a herbicidally or fungicidally effective amount of a compound according to claim 1 and an inert diluent.

13. A herbicidal or fungicidal composition comprising a herbicidally or fungicidally effective amount of a compound according to claim 3 and an inert diluent.

14. A method of combating unwanted vegetation which comprises administering to such vegetatio or to a site from which it is desired to exclude such vegetation a herbicidally effective amount of a compound according to claim 1.

15. The method according to claim 14, wherein such compound is
2-(6-chlorobenzoxazol-2-yl)-N-methyl-oxyacet-2,3-dimethyl-anilide,
2-(6-chlorobenzoxazol-2-yl)-N-methyl-oxyacet-anilide,
2-(6-chlorobenzoxazol-2-yl)-N-ethyl-oxyacet-anilide,
2-(6-chlorobenzoxazol-2-yl)-N-n-propyl-oxyacet-2,3-dimethyl-anilide of the formula,
2-(6-chlorobenzoxazol-2-yl)-N-i-propyl-oxyacet-anilide,
2-(6-chlorobenzoxazol-2-yl)-N-methyl-oxyacet-4-methyl-anilide,
2-(6-chlorobenzoxazol-2-yl)-N-methyl-oxyacet-3-methyl-anilide,
2-(6-chlorobenzoxazol-2-yl)-N-ethyl-oxyacet-3-methyl-anilide or
2-(6-chlorobenzoxazol-2-yl)-N-methyl-oxyacet-2-methyl-anilide.

16. A method of combating fungi which comprises administering to such fungi or to a fungus habitat a fungicidally effective amount of a compound according to claim 1.

17. The method according to claim 16, wherein such compound is
2-(6-chlorobenzoxazol-2-yl)-N-methyl-oxyacet-2,3-dimethyl-anilide,
2-(6-chlorobenzoxazol-2-yl)-N-methyl-oxyacet-anilide,
2-(6-chlorobenzoxazol-2-yl)-N-ethyl-oxyacet-anilide,
2-(6-chlorobenzoxazol-2-yl)-N-n-propyl-oxyacet-2,3-dimethyl-anilide of the formula,
2-(6-chlorobenzoxazol-2-yl)-N-i-propyl-oxyacet-anilide,
2-(6-chlorobenzoxazol-2-yl)-N-methyl-oxyacet-4-methyl-anilide,
2-(6-chlorobenzoxazol-2-yl)-N-methyl-oxyacet-3-methyl-anilide,
2-(6-chlorobenzoxazol-2-yl)-N-ethyl-oxyacet-3-methyl-anilide or
2-(6-chlorobenzoxazol-2-yl)-N-methyl-oxyacet-2-methyl-anilide.

* * * * *

UNITED STATES PATENT AND TRADEMARK OFFICE
CERTIFICATE OF CORRECTION

PATENT NO. : 4,784,682

DATED : November 15, 1988

INVENTOR(S) : Heinz Förster, et al

It is certified that error appears in the above-identified patent and that said Letters Patent is hereby corrected as shown below:

| | |
|---|---|
| Col. 1, line 30 | In the formula delete 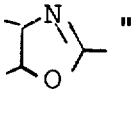 and substitute 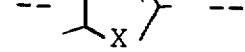 |
| Col. 1, lines 38-39 | Correct spelling of --alkoxyalkyleneoxy-- |
| Col. 2, line 42 | Delete "1 to 2" and substitute --1 or 2-- |
| Col. 2, line 45 | Correct spelling of --substituents-- |
| Col. 2, line 48 | Correct spelling of --halogenoalkoxy-- |
| Col. 2, line 48 | Delete "anad" and substitute --and-- |
| Col. 2, lines 50-51 | Correct spelling of --fluorine-- |
| Col. 14, line 51 | Correct --halogenohydrocarbons-- |
| Col. 14, line 68 | After "oxides," insert --such as, for example, sodium oxide, potassium oxide,-- |
| Col. 15, line 13 | After "-ammoniummethylsulfate," delete "sulfate" |
| Col. 15, line 14 | Delete "C12/C14" and substitute --$C_{12}/C_{14}$-- |
| Col. 15 line 46 | Correct --example-- |
| Col. 15, lines 65-66 | Correct spelling of --Scirpus-- |
| Col. 16, line 15 | Delete "palam" and substitute --palm-- |
| Col. 17, line 3 | After "such as" delete "chlorobenzenes, chloroethylenes or methylenechloride, aliphatic hydrocarbons, such as cyclohexane or paraffins, for example mineral oil fractions, alcohols such as" as it is repeated |
| Col. 17, line 33 | Delete "ther" and substitute --there-- |

UNITED STATES PATENT AND TRADEMARK OFFICE
CERTIFICATE OF CORRECTION

PATENT NO. : 4,784,682
DATED : November 15, 1988
INVENTOR(S) : Heinz Förster, et al Page 2 of 2

It is certified that error appears in the above-identified patent and that said Letters Patent is hereby corrected as shown below:

```
Col. 17, line 42      Delete "asa" and substitute --as--
Col. 18, line 9       Delete "inthe" and substitute
                        --in the--
Col. 18, line 42      Delete "adn" and substitute --and--
Col. 23, line 43      Delete "EXAMPLE 4" and substitute
                        --EXAMPLE 40--
Col. 23, line 56      Correct spelling of --hydroxide--
Col. 25, line 37      Correct spelling of --following--
Col. 26, line 5       Correct spelling of --amount--
Coll 26, line 64      Delete "yound" and substitute
                        --young--
Col. 27, line 67      Delete "cimethyl" and substitute
                        --dimethyl--
Col. 29, line 18      Correct --vegetation--
```

Signed and Sealed this

Twelfth Day of September, 1989

Attest:

DONALD J. QUIGG

Attesting Officer

Commissioner of Patents and Trademarks